United States Patent [19]

Kandel

[11] 3,943,920

[45] Mar. 16, 1976

[54] LARYNGOSCOPE BLADE

[75] Inventor: Ronald E. Kandel, Cupertino, Calif.

[73] Assignee: Ronald E. Kandel, Cupertino, Calif.

[22] Filed: Dec. 6, 1974

[21] Appl. No.: 530,181

[52] U.S. Cl.................................. 128/11; 128/397
[51] Int. Cl........ A61b 1/26; A61b 1/06; A61b 1/24
[58] Field of Search........................... 128/6–11, 397

[56] References Cited
UNITED STATES PATENTS

| | | | |
|---|---|---|---|
| 2,354,471 | 7/1944 | MacIntosh | 128/10 |
| 2,648,329 | 8/1953 | Morch | 128/11 |
| 3,598,113 | 8/1971 | Moore | 128/11 |
| 3,643,654 | 2/1972 | Felbarg | 128/11 |
| 3,856,001 | 12/1974 | Phillips | 128/11 |

*Primary Examiner*—Lawrence Charles
*Attorney, Agent, or Firm*—Lowhurst & Aine

[57] ABSTRACT

A laryngoscope blade includes an upper wall, a lower wall, and a side wall joining the upper and lower walls. The upper wall includes an upper lip engaging portion and an upper gum engaging portion which are contiguous with one another. The lower wall includes a tongue engaging portion and a tip portion disposed for engaging and lifting the epiglottis. The gum portion is substantially parallel to a major extent of the lower wall, whereas the lip portion extends at an acute angle with respect thereto. An inner surface of the upper wall, at the juncture of the gum portion and the lip portion, is provided with a groove and the inner surface of the tip portion is provided with another groove. The bottom surfaces of the grooves are aligned with one another, such that a line of sight extends along such surfaces from each end of the blade.

12 Claims, 5 Drawing Figures

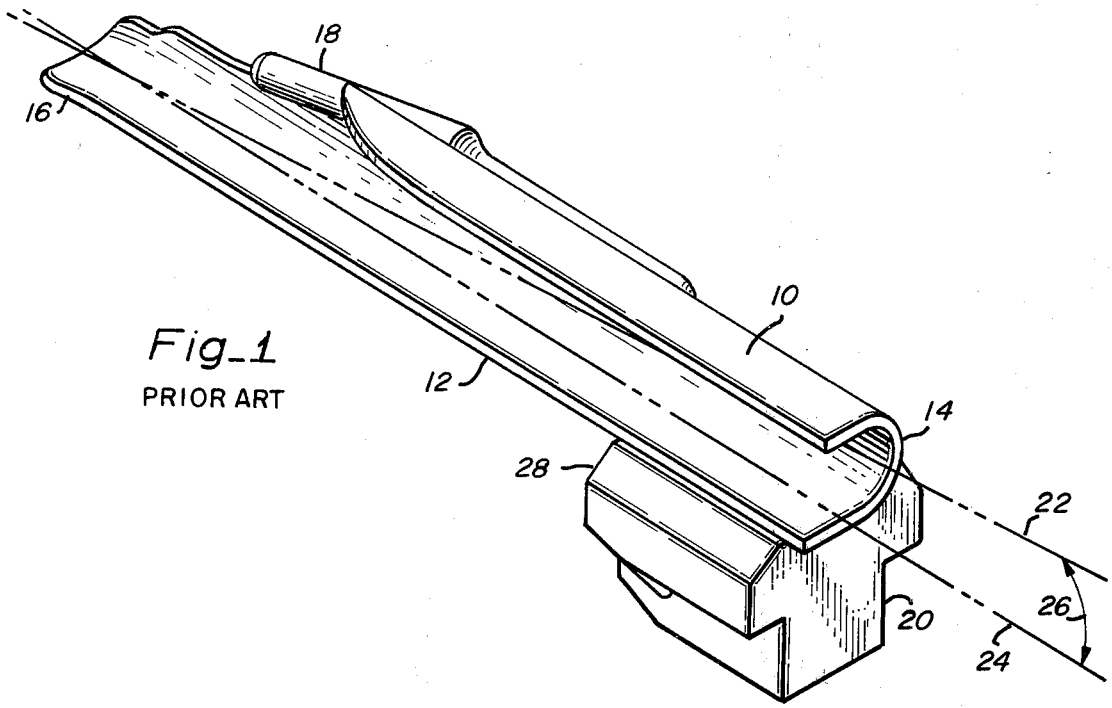
Fig_1
PRIOR ART
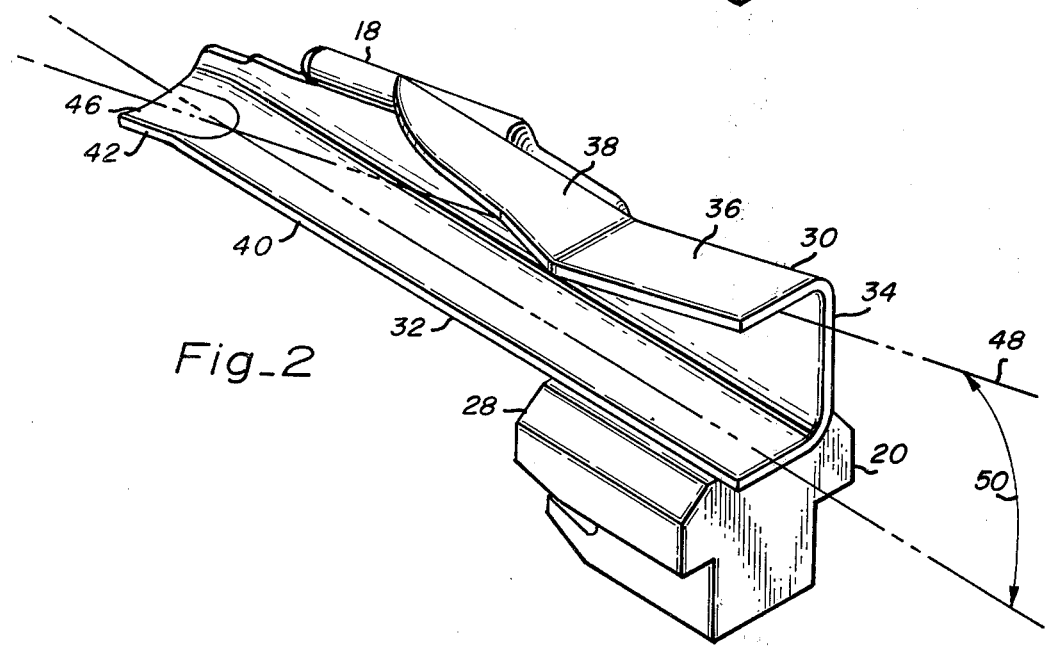
Fig_2

LARYNGOSCOPE BLADE

BACKGROUND OF THE INVENTION

1. Field of the Invention

This invention relates generally to laryngoscopes and more particularly to a laryngoscope blade which provides an increased viewing area.

2. Prior Art

A laryngoscope is an instrument employed for examining the larynx and also serves as an aid for inserting an endotracheal tube through the larnyx into the trachea. Present laryngoscopes employ a blade having a relatively small light source mounted near its tip. The blade has upper and lower walls for maintaining the patients gums spread apart and for depressing the tongue. A tip portion of the lower wall is employed for lifting the epiglottis and the larynx is examined by sighting between the upper and lower walls. When the epiglottis is lifted by the tip portion of the blade, an endotracheal tube can be inserted into the trachea. Usually, the trachea is depressed externally by the physician's fingers so that it is more closely aligned with the patient's mouth, thereby providing a larger viewing area within the larynx.

Examination of the larynx of patients under the age of about 6 months presents a problem not found in older patients. That is, such infant patients have a relatively short neck, inhibiting sufficient head movement to permit the physician to observe a sufficient portion of the larynx. More particularly, the restricted head movement of an infant does not permit as much alignment of the mouth with the trachea as can be obtained in older patients. Presently available laryngoscopes have a relatively narrow field of view. Accordingly, the use of presently available laryngoscope blades for the examination of the larynx of infants does not permit the physician to observe a sufficient amount of the larynx.

When an endotracheal tube is being inserted into the trachea by the physician, the physician's one hand must hold and manipulate the laryngoscope while the other hand is holding and inserting the endotracheal tube. As mentioned above, it is often necessary for the physician to externally depress the trachea to more closely align it with the mouth opening while inserting such an endotracheal tube. In order to perfrom all of these functions, the physician must employ some fingers of the hand holding the laryngoscope to externally depress the trachea. However, presently available laryngoscope blades are either too short, such that they cannot be employed for reaching the epiglottis of all patients, or are too long, such that the dual functions mentioned above cannot be performed by the same hand.

SUMMARY OF THE INVENTION

Accordingly, it is a primary object of the present invention to provide a laryngoscope blade which has a relatively large field of view.

Another object of the present invention is to provide a laryngoscope blade which is optimally dimensioned for use with infant patients.

Still another object of the present invention is to provide a laryngoscope blade which is dimensioned to permit the user thereof to employ the same hand which is holding the laryngoscope to externally depress the patient's trachea.

These and other objects of the present invention are attained by a laryngoscope blade which is flared at its viewing end to provide a larger field of view. That is, the laryngoscope blade of the present invention includes an upper wall and a lower wall, with the upper wall being formed of an upper lip engaging portion and an upper gum engaging portion which are contiguous with one another and the lower wall including a tip portion disposed for engaging and lifting the epiglottis. The upper gum engaging portion is substantially parallel to a major extent of the lower wall, whereas the upper lip engaging portion extends at an acute angle with respect to the lower wall, and such acute angle is dimensioned such that a line of sight exists from the viewing end of the blade along an inner surface of the juncture between the upper lip portion and the upper gum portion to an inner surface of the tip portion of the lower wall. This configuration provides the maximum field of view within the patient's larynx.

A feature of the present invention resides in the provision of grooves along the internal surfaces of the blade which lie along a line at the extreme end of the field of view, thereby increasing that field of view.

Another feature of the present invention resides in the provision of gum engaging surfaces which are relatively large in comparison to those of prior known laryngoscope blades to reduce the possibility of damage to the patient's gums.

It can be appreicated that the laryngoscope blade of the present invention provides a distinct advantage to the physician by increasing the field of view within the larynx by a considerable factor. As will be appreciated from the following description, this field of view in the laryngoscope blade of the present invention is increased more than twice that of prior known laryngoscope blades. Furthermore, the physician is provided with the advantage of being able to employ the same hand for holding and manipulating the laryngoscope and to externally depress the trachea.

These and other objects, features and advantages of the present invention, however, will be more fully realized and understood from the following detailed description, when taken in conjunction with the accompanying drawings, wherein:

BRIEF DESCRIPTION OF THE DRAWINGS

FIG. 1 is a view in perspective of a known prior art laryngoscope blade.

FIG. 2 is a view in perspective of a laryngoscope blade constructed in accordance with the principles of the present invention.

Like reference numerals throughout the various views of the drawings are intended to designate the same elements.

DETAILED DESCRIPTION OF THE PREFERRED EMBODIMENT

Figure 3:
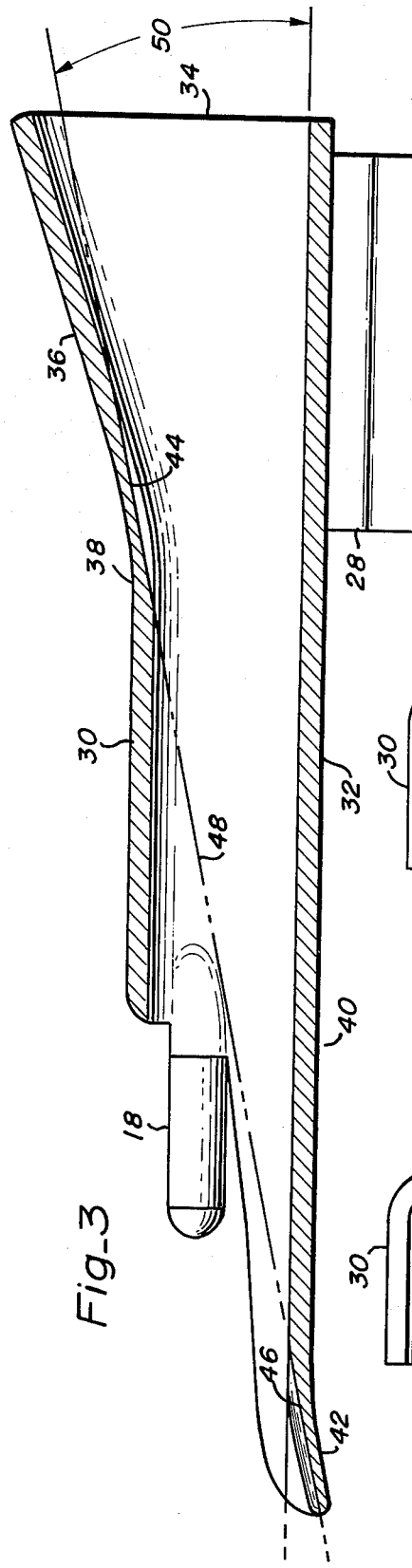
FIG. 3 is a side view, partially in section, of the laryngoscope blade illustrated in FIG. 2.

U.S. Pat. No. 2,433,705 discloses a laryngoscope which includes a handle for housing one or more batteries, and a blade which is removably attached to the handle. The commercial embodiment of the blade disclosed in that patent is illustrated in FIG. 1 and represents one of the closest known prior art to the laryngoscope blade of the present invention. As shown in FIG. 1, the blade includes an upper wall 10, a lower wall 12 and a side wall 14. The lower wall 12 terminates in a tip portion 16 which is disposed for engaging and lifting the epiglottis, which is a layer of tissue extending over and guarding the opening of the larynx. In use the blade is inserted into a patient's mouth and the epiglottis is lifted by tip portion 16 so that the physician can sight between the upper and lower walls 10 and 12 to examine the larynx. A light source 18 mounted on the side wall 14 illuminates the area under examination. A head 20 is disposed for being mounted on a handle (not shown) which contains a source of electrical energy to energize the light source 18.

When the laryngoscope is to be employed for examining the larynx, the patient's head is rotated to its maximum limit, without causing injury to the patient, in a direction to align the mouth opening with the larynx as closely as possible. Thereafter, when the laryngoscope blade is inserted, the upper wall 10 is placed in contact with the patient's upper gum or teeth and the tip portion 16 engages and lifts the epiglottis. A field of view is then presented to the physician, with one edge of that field of view being defined by a phantom line in FIG. 1 designated with the reference numeral 22. The line of sight represented by the line 22 extends from an inner edge of the end of the upper wall 10, at the viewing end of the blade, to and tangentially across an inner surface of the tip portion 16. The angle of the line 22 with respect to a line 24 extending across the inner surface of the lower wall 12, which angle is represented by the reference numeral 26, is approximately equal to 5°, and is no greater than 6°.

Because of the relatively short neck in infants, the head cannot be rotated as far as it can with older patients. As a result, if the same blade is employed for patients of all age brackets, the physician will have a smaller field of view when examining an infant patient with such a blade.

In order to bring more of the larynx into the field of view, it is a common practice to externally depress the trachea so that it becomes more closely aligned with the mouth opening. The distance between the gums and the epiglottis varies from patient to patient and is generally greater in older patients. Accordingly, if a relatively long laryngoscope blade is employed for examining the larynx of an infant patient, the physician cannot employ the same hand for holding the laryngoscope and for depressing the trachea. In the laryngoscope blade illustrated in FIG. 1, the distance from an edge 28 of the head 20 to the end of the tip portion 16 is approximately 76 mm, whereas the optimum distance between these two points for infant patients is approximately 58mm.

The laryngoscope blade of the present invention overcomes the above mentioned disadvantages by dimensioning the length of the blade so that it more closely conforms to the appropriate anatomical structure of infants and by increasing the field of view through the blade. As shown in FIGS. 2 and 3, the laryngoscope blade of the present invention includes an upper wall 30, a lower wall 32 and a side wall 34. The upper wall 30 includes an upper lip engaging portion 36 and an upper gum engaging portion 38 which are contiguous with one another. The lower wall 32 includes a tongue engaging portion 40 and a tip portion 42 for engaging and lifting the epiglottis. Light source 18 is mounted on and extends from the side wall 34 to provide illumination to the area being examined. The lower wall 32 is mounted on the head 20 which is, in turn, disposed for being mounted on a handle as mentioned above.

A groove 44 is provided in an inner surface of the upper wall 30 at the juncture of the lip portion 36 and gum portion 38. A second groove 46 is provided in an inner surface of the tip portion 42. It can be appreciated from FIG. 3 that the gum portion 38 is substantially parallel to a major extent of the lower wall 32, whereas the lip portion 36 extends at an acute angle with respect to the lower wall 32. This angle is shown in FIG. 3 as being equal to 18°. The tip portion 42 also extends at an angle with respect to the tongue portion 40 as shown in FIG. 3. Surfaces of the grooves 44 and 46 are aligned with one another, such that a line of sight 48 extends across such surfaces and is at an acute angle with respect to the lower wall 32, which angle is designated with the reference numeral 50. The acute angle 50 is equal to approximately 12°.

Figure 5:
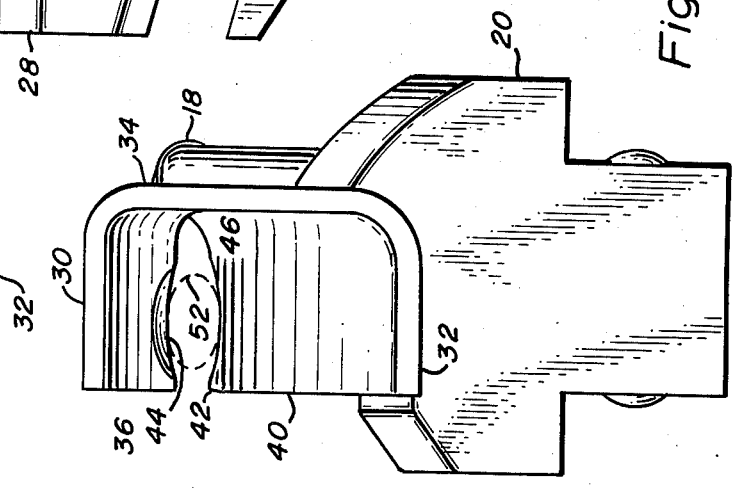
FIG. 5 is an end view similar to that of FIG. 4 of the laryngoscope blade of the present invention, but rotated to illustrate the increased field of view which is attained thereby.
Figure 4:
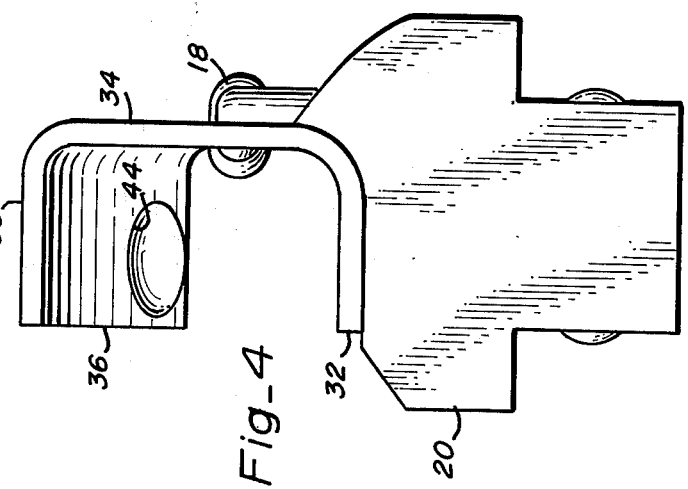
FIG. 4 is an end view of the laryngoscope blade illustrated in FIG. 3.

FIG. 4 illustrates an end view of the laryngoscope blade of the present invention with a line of sight of the observer being parallel to the lower wall 32. When the observer is provided such a line of sight as depicted in FIG. 4, the larynx opening is partially hidden from view. However, when the observer is positioned so that his line of sight is at an acute angle of approximately 8° with respect to the lower wall 32, his view will be that as shown in FIG. 5 of the drawings. As shown therein, a dotted line 52 represents the larynx opening. It can be appreciated from the drawing that such an 8° line of sight with respect to the lower wall 32 provides a complete view of the larynx opening with the laryngoscope blade of the present invention, whereas such an 8° line of sight with prior known blades would completely obscure the opening. As mentioned above, a line of sight of 6° with respect to the lower wall with prior known laryngoscope blades would be the limit at which the view would be occulted.

In a constructed embodiment of the present invention, the thickness of the walls 30, 32, and 34 was 0.070 inch and the thickness of the material at the bottom of the grooves 44 and 46 was 0.025 to 0.030 inch. The distance from the edge 28 to the end of the tip portion 42 was 58 mm. It is to be understood, however, that this distance may be in the range of 53 mm to 68 mm. The critical dimension is the distance from the juncture of the lip portion 36 and the gum portion 38 to the end of the tip portion 42. This dimension should be in the range of 55 mm to 70 mm, with 60 mm being preferable. If this distance is decreased below 60 mm, the lip portion 36 will, with some infant patients, act as a wedge against the patient's upper gum. As this distance is increased above 60 mm, the field of view is decreased.

When it is necessary to employ the laryngoscope blade, the time required to lift the epiglottis and insert an endotracheal tube is often essential, since the patient is usually not breathing. The laryngoscope blade of the present invention permits the physician to perfrom that operation in a minimum amount of time, since the field of view is considerably greater than that found in prior known laryngoscope blades. Furthermore, when the epiglottis has been lifted by the tip portion 42, the physician can employ the fingers of the same hand which is holding the blade to depress the trachea so that an endotracheal tube can be inserted therein with greater facility. It can also be appreciated from the drawings that the upper gum portion 38 is wider than that found in prior known blades so as to reduce the possibility of damage to the patient's gums and teeth.

The invention claimed is:

1. A laryngoscope blade comprising an upper wall, a lower wall, and a side wall joining said upper and lower walls; said upper wall including an upper lip engaging portion and an upper gum engaging portion contiguous with one another; said lower wall including a tip portion disposed for engaging and lifting the epiglottis; said upper lip engaging portion overlying and extending at an acute angle with respect to a major extent of said lower wall and said upper gum portion overlying and being substantially parallel to a major extent of said lower wall; said acute angle being dimensioned such that a direct line of sight exists from one end of said walls along an inner surface of the juncture between said upper lip portion and said upper gum portion to an inner surface of said tip portion.

2. The laryngoscope blade of claim 1, wherein said lower wall further includes a tongue engaging portion which is contiguous with said tip portion and is substantially parallel to said upper gum engaging portion; said tip portion being at an angle with respect to said tongue engaging portion which is approximately equal to the compliment of said acute angle.

3. The laryngoscope blade of claim 1, wherein the inner surface of said juncture between said upper lip portion and said upper gum portion includes a concavity, such that the thickness of a portion of the material of said juncture is reduced in comparison to any contiguous material, and the inner surface of said concavity is positioned along and is parallel to said line of sight.

4. The laryngoscope blade of claim 1, wherein the inner surface of said tip portion includes a concavity, such that the thickness of a portion of the material of said tip portion is reduced in comparison to any contiguous material, and the inner surface of said concavity is positioned along and is parallel to said line of sight.

5. The laryngoscope blade of claim 1, wherein the inner surface of said juncture between said upper lip portion and said upper gum portion includes a first concavity, such that the thickness of a portion of the material of said juncture is reduced in comparison to any contiguous material, and wherein the inner surface of said tip portion includes a second concavity, such that the thickness of a portion of the material of said tip portion is reduced in comparison to any contiguous material, and the inner surfaces of said first and second concavities are positioned along and are parallel to said line of sight.

6. The laryngoscope blade of claim 5, wherein said lower wall further includes a tongue engaging portion which is contiguous with said tip portion and is substantially parallel to said upper gum engaging portion; said tip portion being at an angle with respect to said tongue engaging portion which is approximately equal to the compliment of said acute angle.

7. The laryngoscope blade of claim 6, wherein the minimum thickness of the material at said first and second concavities is no more than 0.030 inch.

8. The laryngoscope blade of claim 6, wherein the angle between said line of sight and said lower wall is in the range of 10° to 15°.

9. The laryngoscope blade of claim 8, wherein the angle between said line of sight and said lower wall ie equal to approximately 12°.

10. The laryngoscope blade of claim 8, wherein said acute angle is greater than the angle between said line of sight and said lower wall.

11. The laryngoscope blade of claim 1, wherein said lower wall further includes a tongue engaging portion which is contiguous with said tip portion and is substantially parallel to said upper gum portion; and wherein the length of said tongue portion and said tip portion is in the range of 53 to 68 mm.

12. The laryngoscope blade of claim 11, wherein the length of said tongue portion and said tip portion is equal to approximately 58 mm.

* * * * *